United States Patent [19]

Flax

[11] Patent Number: 4,587,973

[45] Date of Patent: May 13, 1986

[54] ULTRASONIC METHOD AND MEANS FOR MEASURING BLOOD FLOW AND THE LIKE USING AUTOCORRELATION

[75] Inventor: Stephen W. Flax, Waukesha, Wis.

[73] Assignee: General Electric Company, Milwaukee, Wis.

[21] Appl. No.: 754,193

[22] Filed: Jul. 10, 1985

Related U.S. Application Data

[63] Continuation of Ser. No. 520,959, Aug. 8, 1983, abandoned.

[51] Int. Cl.⁴ .............................................. A61B 10/00
[52] U.S. Cl. .................................. 128/663; 73/861.25
[58] Field of Search .............................. 128/660, 663; 73/861.06, 861.25

[56] References Cited

U.S. PATENT DOCUMENTS

| | | | |
|---|---|---|---|
| 3,844,170 | 10/1974 | Critten | 73/861.06 |
| 3,940,731 | 2/1976 | Cooper et al. | 128/663 |
| 4,109,644 | 8/1978 | Kojima | 128/660 |
| 4,201,083 | 5/1980 | Kurita et al. | 73/861.06 |

Primary Examiner—Kyle L. Howell
Assistant Examiner—Ruth S. Smith
Attorney, Agent, or Firm—Flehr, Hohbach, Test, Albritton & Herbert

[57] ABSTRACT

Blood flow measurements are obtained by determining changes in time varying textural patterns of reflected ultrasonic waves from the blood flow at a predetermined position in a blood vessel. Electrical signals generated in response to reflected ultrasonic waves from moving blood cells are autocorrelated to indicate changes in the textural patterns.

4 Claims, 4 Drawing Figures

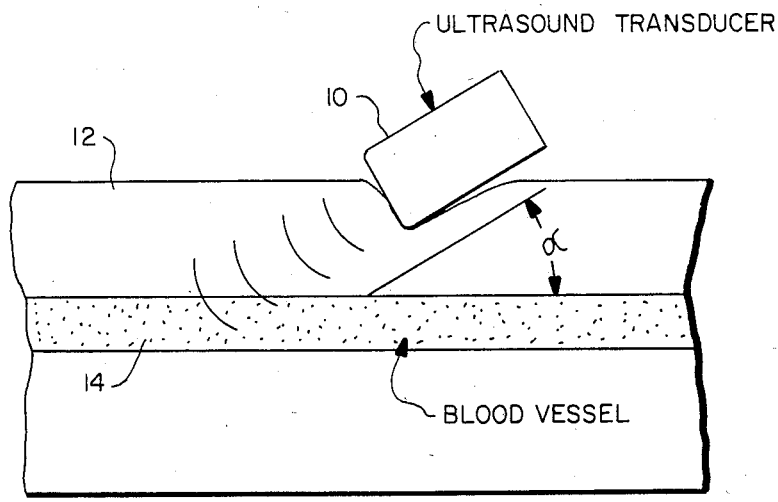
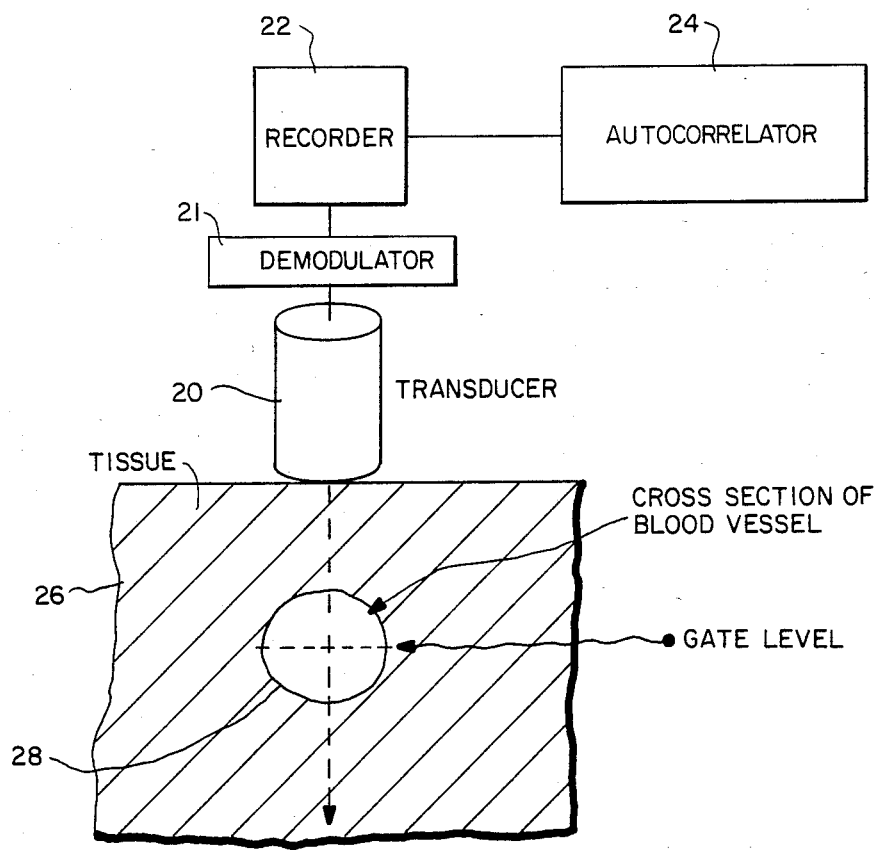

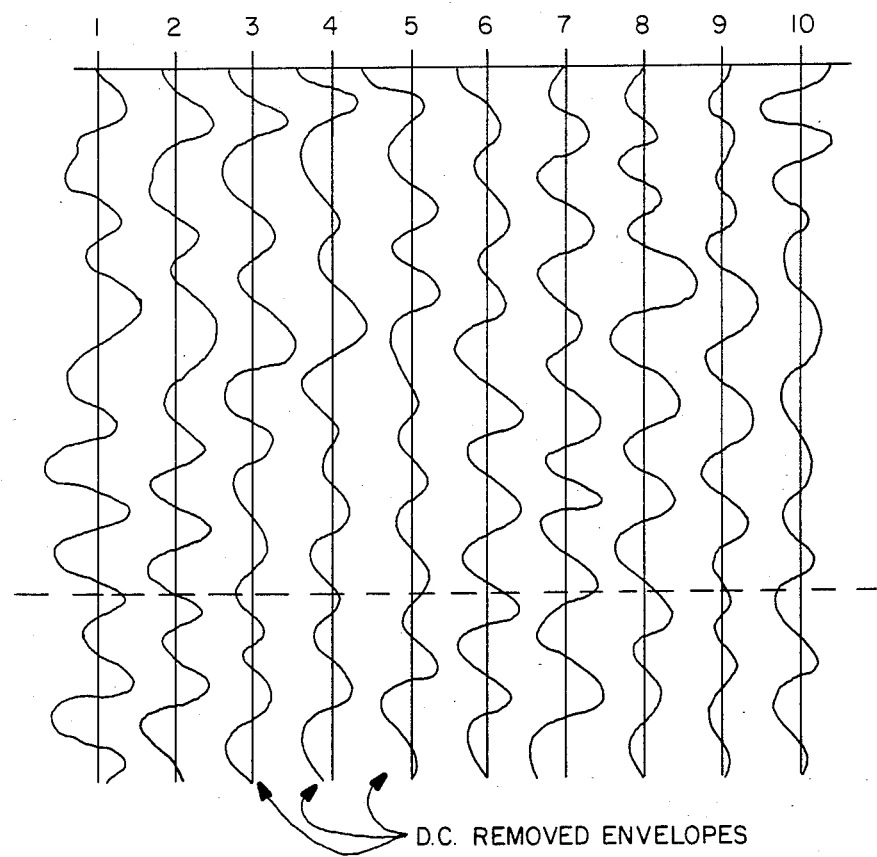
FIG.—3A
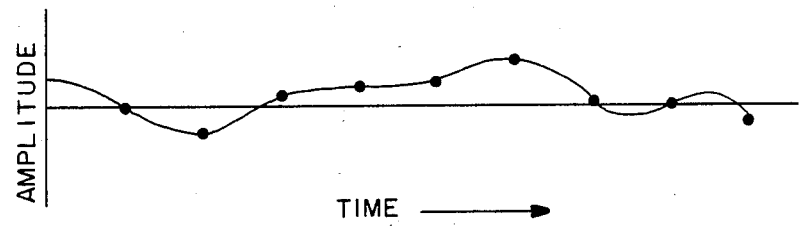
FIG.—3B

ULTRASONIC METHOD AND MEANS FOR MEASURING BLOOD FLOW AND THE LIKE USING AUTOCORRELATION

This is a continuation of application Ser. No. 520,959 filed Aug. 8, 1983, now abandoned.

This invention relates generally to flow measurements, and more particularly the invention relates to blood flow measurements using ultrasonic and autocorrelation techniques.

Blood flow measurements have been estimated by measuring Doppler frequency shifts in ultrasonic signals reflected from moving blood cells. However, the technique has limited accuracy because the angle between the blood flow and the ultrasonic transducer is critical and must be estimated. Further, the necessary electronic circuitry for detecting and measuring frequency shift in the reflected ultrasonic waves is complex and expensive. Moreover, there are relatively severe limitations on the sampling rate needed to yield the necessary spectral data.

Heretofore, it is known in sonar technology that velocity measurements can be obtained by a cross correlation technique. By employing two or more separated transducers, sonar signals reflected from a volume of scatterers can be corss correlated to determine the velocity of the volume of scatterers. See, for example, U.S. Pat. No. 4,244,026 to Frank Dickey.

As reported by Flax, Glover, and Pelc in "Textural Variations in B-Mode Ultrasonography: A Stochastic Model", *Ultrasonic Imaging* 3, pgs. 235–257 (1981) textural patterns of reflected ultrasonic waves are predictable as a function of distance or depth for a stochastic scattering site. That is, the textural pattern at a given depth in tissue will remain statistically the same. Thus, in a normal B-mode scan the textural pattern is generated spatially by translating the transducer across the tissue surface. If the transducer is held stationary instead of being translated, the return signal will remain basically constant due to the fact that the stochastic scattering sites are stationary in space. However, if the transducers were held stationary but the tissue sample is allowed to move then the returning signal will vary as a function of time. The rate of change of that signal would in turn be functionally related to the velocity of movement of the tissue sample.

In accordance with the present invention velocity measurements of a volume of scatterers are obtained by using a single transducer to obtain temporal textural pattern variations resulting from the movement of the volume of scatterers. By autocorrelation of the textural pattern measurements, the velocity of the volume of scatterers is obtained.

Accordingly, an object of the invention is an improved method of measuring blood flow and the like.

Another object of the invention is flow measurement apparatus which is relatively simple.

A feature of the invention is the determination of a measurement of textural patterns of a moving scattering medium.

The invention and objects and features thereof will be more readily apparent from the following detailed description and appended claims when taken with the drawings, in which:

FIG. 1 is an illustrative representation of blood flow measurements using Doppler techniques.

FIG. 2 is an illustrative representation of blood flow measurements using apparatus in accordance with the present invention.

FIG. 3A is a plot of reflected ultrasonic signals for a scattering medium.

FIG. 3B is a plot of amplitude of the reflected signals of FIG. 3A at a fixed depth in the scattering medium.

Referring now to the drawings, FIG. 1 is a representation of blood flow measurement by determining Doppler frequency shifts in ultrasonic signals reflected from moving blood cells. As shown, an ultrasound transducer 10 is aligned at an angle α on the surface of a tissue body 12 in which a blood vessel 14 is located. Ultrasonic signals transmitted by the transducer 10 are reflected by the blood flow in vessel 14 and received by the transducer 10. By measuring the Doppler shift in frequency of the reflected waves, the particle velocity can be obtained using the following equation:

$$\text{Doppler shift} = (2F_e\, V \cos \alpha)/C$$

where $F_e$ = Frequency of excitation
$V$ = Particle Velocity
$\alpha$ = Angle between acoustical axes
$C$ = Velocity of sound As noted above and as evident from the Doppler shift equation, the angle between the blood flow and the ultrasonic transducer is critical to the accuracy of the blood flow determination based upon Doppler shift. As further noted above, the complexity of the required electronic circuitry and the smapling rate needed to yield the necessary spectral data are further limitations on the doppler shift technique.

FIG. 2 is a functional block diagram of apparatus in accordance with the present invention for measuring blood flow. In this embodiment the transducer 20 is connected to a recorder 22, through the modulator 21 which records the demodulated electrical signals produced by the demodulator 21 in response to reflected ultrasonic waves. The recorder 22 is connected to an autocorrelation 24 which is able to provide a measure of blood flow from the signals of recorder 22, as will be described further hereinbelow. The transducer 20 is positioned on the surface of tissue 26 above a blood vessel 28. Ultrasonic waves are transmitted through the tissue 26 and vessel 28, and transducer 20 generates electrical signals in response to reflected waves as illustrated in FIG. 3A. In FIG. 3A ten samples are illustrated of the demodulated electrical signals from transducer 20 which are recorded by the recorder 22. The autocorrelation 24 correlates the signals corresponding to a specific depth in tissue 26 such as the central position within vessel 28, and a correlation over time of the signals from this depth produces a measurement of movement of the scatterers. For example, using a gate level at the center of vessel 28, as indicated in FIG. 2 and in FIG. 3A, the variation in signal amplitude with time can be produced as illustrated in FIG. 3B. The change in signal amplitude, indicative of the change in scatter texture of the moving scatterers, is then autocorrelated with the resulting function being related to blood flow.

The invention is readily implemented using conventional apparatus and provides a measure of blood flow which is less dependent on transducer angle. While the invention has been described with reference to a specific embodiment and application, the description is illustrative of the invention and is not to be construed as limiting the invention. Various modifications and applications may occur to those skilled in the art without departing from the true spirit and scope of the invention as defined by the appended claims.

What is claimed is:

1. A method of measuring fluid flow from changes in textural patterns of reflected ultrasonic wave comprising the steps of transmitting ultrasonic signals into said fluid flow at a first position from a stationary transducer oriented perpendicular to said fluid flow, receiving reflected ultrasonic signals reflected from said fluid flow with said stationary transducer which generates electrical signals in response thereto, demodulating said electrical signals to obtain demodulated electrical signals indicative of textural pattern and autocorrelating said demodulated electrical signals whereby fluid flow at a fixed position in said fluid flow is obtained from changes in said textural patterns.

2. The method as defined by claim 1 wherein said steps of transmitting and receiving are performed with the same transducer.

3. The method as defined by claim 1 wherein said step of autocorrelating said demodulated electrical signals includes detecting and comparing amplitudes of said signals from said fixed position as a function of time.

4. Apparatus for use in measuring flow of a fluid such as blood and based on changes in textural pattern of reflected ultrasonic wave comprising an ultrasonic transducer for transmitting ultrasonic waves perpendicularly into said flow of fluid, receiving ultrasonic signals reflected by said fluid, and producing electrical signals indicative of said received ultrasonic signals, means for detecting textural pattern signals from said electrical signals, means for recording said textural pattern signals, and means for autocorrelating the recorded textural pattern signals thereby indicating change in textural patterns as function of time at a given position as a measure of said fluid flow.

* * * * *

UNITED STATES PATENT AND TRADEMARK OFFICE
CERTIFICATE OF CORRECTION

PATENT NO. : 4,587,973
DATED : May 13, 1986
INVENTOR(S) : Stephen W. Flax

It is certified that error appears in the above-identified patent and that said Letters Patent is hereby corrected as shown below:

Column 1, line 27, delete "corss: and insert --cross--.

Column 2, line 31, delete "smapling" and insert --sampling--.

Column 2, line 41, delete "autocorrelation" and insert --autocorrelator--.

Column 2, line 51, delete "autocorrelation" and insert --autocorrelator--.

Column 4, line 20, delete "change" and insert --changes--.

Column 4, line 21, after "as" insert --a--.

Signed and Sealed this

Twenty-first Day of October, 1986

[SEAL]

*Attest:*

DONALD J. QUIGG

*Attesting Officer*  *Commissioner of Patents and Trademarks*